United States Patent [19]

Joliot et al.

[11] Patent Number: 4,696,570
[45] Date of Patent: Sep. 29, 1987

[54] SPECTROPHOTOMETER WITH STATISTICALLY BALANCED LIGHT FOR VERY HIGH RESOLUTION

[75] Inventors: A. Pierre Joliot, Antony; Daniel Beal, Orsay, France

[73] Assignee: Centre National de la Recherche Scientifique (C.N.R.S.), Paris, France

[21] Appl. No.: 728,295

[22] Filed: Apr. 29, 1985

[30] Foreign Application Priority Data

Apr. 23, 1985 [FR] France ................. 85 06172

[51] Int. Cl.⁴ .................................................. G01J 3/42
[52] U.S. Cl. ...................................... 356/319; 356/334
[58] Field of Search ........ 356/300, 319, 320, 323–325; 250/200, 215, 216, 578

[56] References Cited

U.S. PATENT DOCUMENTS

| | | | |
|---|---|---|---|
| 3,569,721 | 3/1971 | Goldberg | 356/321 X |
| 4,099,872 | 7/1978 | White | 356/319 X |
| 4,241,998 | 12/1980 | Farkas et al. | 356/319 |
| 4,566,792 | 1/1986 | Suzuki | 356/319 |

FOREIGN PATENT DOCUMENTS 7507048 10/1978 France .

OTHER PUBLICATIONS

Joliot P., et al, "Une Nouvelle Méthod Spectrophotométrique Destinée à létude Des Réactions Photosynthétiques", *Journal de Chimie Physique* 1980, 77, No. 3.
Joliot P. et al, "Electron Transfer Between the Two Photosystems, I. Flash Excitation Under Oxidizing Conditions" *Biochimica et Biophysica Acta* 765 (1984) 210–219 Elsevier.

*Primary Examiner*—Eugene R. LaRoche
*Assistant Examiner*—David Mis
*Attorney, Agent, or Firm*—Staas & Halsey

[57] ABSTRACT

A flash tube (1) illuminates the inlet slit diaphragm of a monchromator illuminator (3) the outlet slit diaphragm of which is applied to an optical conductor (5) forming a statistically balanced derivation towards a measuring cell (6M) and a reference cell (6R). Quantic photodetectors (7M and 7R) measure respectively the light conveyed by the two cells. The electric signals obtained are amplified and digitalized, and a microcomputer (9) calculates the relation between the measuring signal (M) and the reference signal (R), other things being equal.

15 Claims, 8 Drawing Figures

SPECTROPHOTOMETER WITH STATISTICALLY BALANCED LIGHT FOR VERY HIGH RESOLUTION

BACKGROUND OF THE INVENTION

The invention concerns spectrophotometry, i.e. the study of optical transmission properties of substances.

Among the known applications of spectrophotometry, the study of biological media (capable of photosynthesis) which strongly diffuse light, is a particularly delicate one. Its progress is limited by the analysis apparatus available to the experimenter, and more particularly by the spectrophotometers, as is indicated in the following publications:

"Une nouvelle méthode spectrophotométrique destinée à l'étude des réactions photosynthétiques", Pierre Joliot, Daniel Béal and Bernard Frilley; Journal de Chimie Physique, 1980, 77, No. 3.

"Electron Transfer between the two photosystems, I. Flash Excitation under oxidizing conditions", Pierre Joliot and Anne Joliot, Biochimica et Biophysica Acta, 765 (1984) 210-219 Elsevier.

In most high performance applications, the spectrophotometers operate in a differential mode. This means that the measurement of the optical transmission coefficient is done simultaneously on a measurement sample and on a reference sample. More generally, it is conceivable to produce a differential measure between two working samples which undergo different conditions. It is therefore known to use a differential spectrophotometer which includes a monochromatic measuring light source, more especially in the form of monochromatic flashes of short duration, an optical feeder to apply this light to both samples at the same time, as well as two photodetectors to selectively receive the light transmitted through each one of the two samples, during the operation of the measuring light source in order to compare the behavior of these two samples, as described in the abovementioned paper in Journal de Chimie Physique.

The performance of a spectrophotometer is mainly determined by its resolution, which depends upon numerous factors.

The permanent goal of persons skilled in the art is therefore to improve this resolution.

The very particular field of biological studies with respect to photosynthesis is the subject of specific limitations, namely regarding the intensity of the measuring light. This results in differences between this particular application and the other applications of spectrophotometers.

The publication in the Journal de Chimie Physique mentioned above, describes an instrumental technique used for studying the photosynthetic reactions, and includes useful instructions for improving the resolution.

SUMMARY OF THE INVENTION

An object of this invention is thus to provide a very high resolution spectrophotometer, to be used in other fields than that of biological studies on photosynthesis.

The proposed spectrophotometer is of the type which includes two sample locations, optical means for applying to both samples a monochromatic measuring light, photodetectors for selectively collecting the light trasmitted through each of the samples, as well as electronic means for comparing the transmitted light quantities thus measured by both photodetectors.

According to a general feature of this invention, the optical means distributes the measuring light to both samples in a statistically balanced way. This apparently simple object is in practice rather difficult to fulfill.

It is possible to accomplish it using optical means including a flash source, which lights the inlet slit diaphragm of a monochromator with a holographic concave grid.

The statistical balance is then obtained by the use of a parallelepipedic light guide, optically coupled to the outlet slot of the monochromator, and followed by a light guide in a "Y" shape, the optical fibers of which are substantially randomly distributed towards its two branches.

Preferably the flash source is connected to the inlet slit diaphragm of the monochromator by an optical fiber beam with a substantially random distribution, followed by a parallelepipedic light guide. This further improves the statistical balance of the light applied to both samples.

According to another aspect of the invention, the monochromator is designed with many inlet slit diaphragms respectively coupled by optical fiber beams to one or more flash tubes, in order that various beams of neighboring wavelengths be available at the outlet slit diaphragm of the monochromator. The selection is made naturally by operating the flash tubes. It will be further observed that with such an assembly, flashes can be performed at very short intervals if many flash tubes are used, since the constraint induced from the minimal period between two consecutive flashes of one tube no longer plays any role.

It is then preferable that at least some of the light guides located at the inlet of the monochromator include an angle deflector, preferably in the form of a guide face at 45°, with an outer metal coating.

It is also advantageous, in such a case, that the inlet slit diaphragms of the monochromator be essentially defined by the light guide, instead of using the customary diaphragm devices which form a transversally mobile slit.

According to another aspect of the invention, light detectors are large surface silicium photodiodes for collecting the light transmitted through a solid angle and with a high quantum yield.

According to another aspect of the invention, the photodiodes are sensitive to wavelengths ranging from ultraviolet to near-infrared. The device is then specially interesting as it is possible to operate on a rather wide range of wavelengths, without changing either the flash sources, the monochromator, or the photodetectors.

In a particular embodiment, the electronic means includes current-voltage converting means, associated with double filtering means which have a low-pass effect under a frequency of about 100 kHz, and a high-pass effect over a frequency of about one kilohertz.

In practice, the electronic means further includes, for every measurement, a sampling and holding device associated with an analog-to-digital converter, the whole set being each time controlled by a retardation circuit which receives a synchronizing pulse coming from the flash source.

These electronics means are advantageously completed by calculation means which receive the outputs of the two analog-to-digital converters to determine therefrom a ratio which is then subjected to numerical treatments including the comparison of the ratio to a reference value of the ratio, a so-called base line, which represents a reference state of both samples.

One of the samples is usually a working sample, whereas the other one is a reference sample.

It is then preferable that the current-voltage converter, associated with the reference sample, should work on the only output of the corresponding photodetector, whereas the current-voltage converter corresponding to the working sample, operates on the (amplified) difference between the output of the photodetector associated with the working sample, and the output of the photodetector associated with the reference sample.

The device is suitable for photochemical measurement, for which the samples are further submitted to the action of a stimulating light.

Samples can be held in cells preferably designed in such a way that their walls form light guides, at least for the measuring light.

A particular advantageous cell is obtained by providing a metal cell on one side with a window through which photochemical stimulating light can pass.

BRIEF DESCRIPTION OF THE DRAWINGS

Other characteristic features and advantages of the invention will appear when looking over the detailed description given hereafter, as well as the accompanying drawings, in which.

DESCRIPTION OF THE PREFERRED EMBODIMENTS

Some aspects of the invention require the use of geometrical data, which can only be completely defined by drawings. Consequently, the drawings are integrated into the description and not only to be used as a completion of the description but also in order to define the invention.

Figure 1:
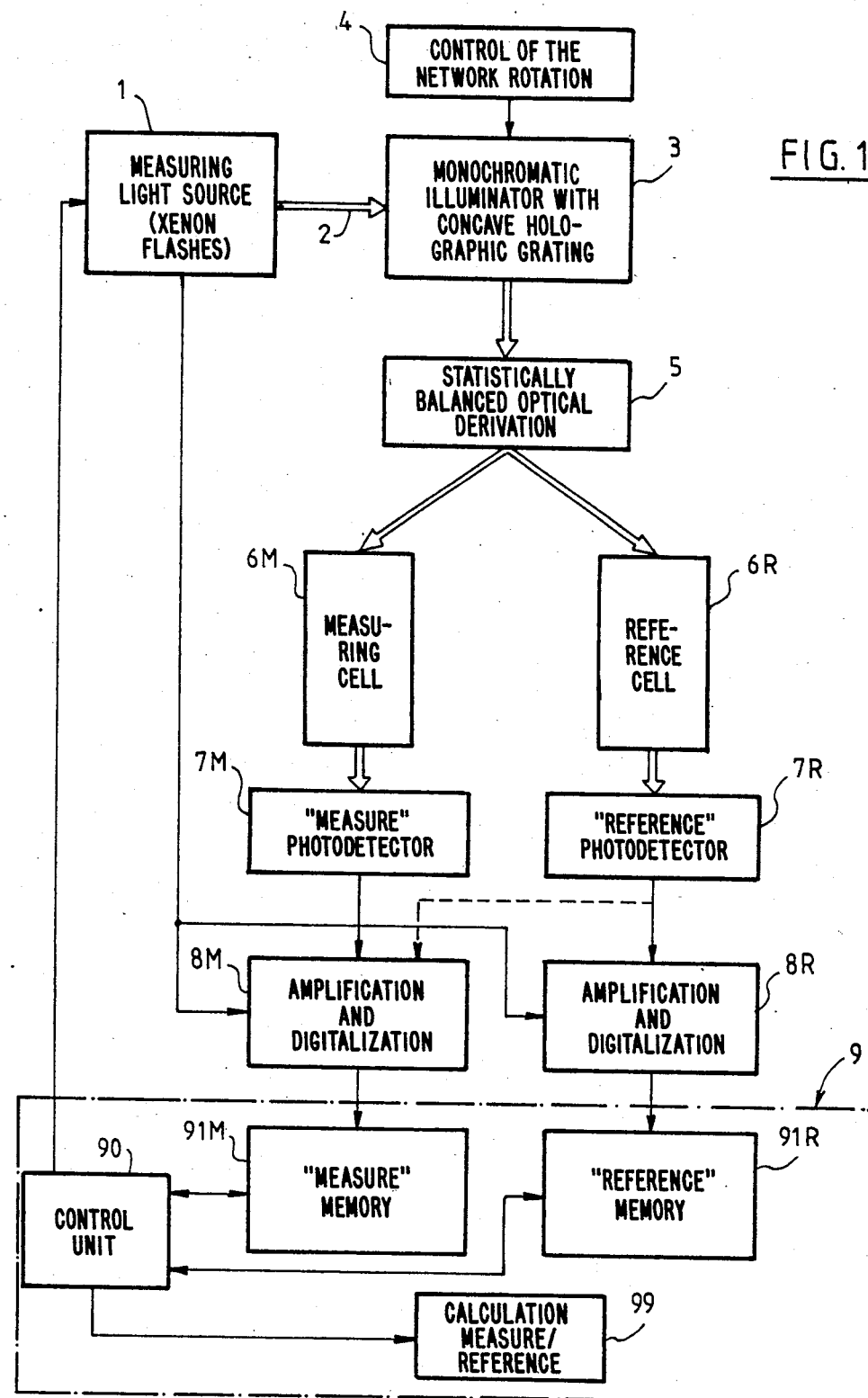
FIG. 1 is a principle schematic representation of a device according to the invention.

In FIG. 1, a monochromatic light source is defined by a xenon flash tube 1, the output of which is applied by an optical conductor 2 to the inlet slit diaphragm of a monochromator 3.

An outlet slit diaphragm of the monochromator is connected to an optical conductor 5 forming a statistically balanced derivation, the two outputs of which are connected to a measuring cell 6M and a reference cell 6R respectively.

As mentioned above, it is usual in biological experimentation to use a working sample and a reference sample. But the invention could also apply to making differential measures between two working samples.

The outputs of the instruments 8M and 8R are thus two sets of digital signals proportional to the numbers of photoelectrons detected by detectors 7M and 7R, provided that the instruments 8M and 8R have been correctly arranged.

A digital electronic circuit 9, which can be based on a microcomputer, includes memory zones 91M and 91R for receiving digital measuring and reference signals respectively.

The microcomputer 9 is connected to the light source 1, in order to control the timings of production of the measuring light flashes.

After each flash, the control unit 90 of the microcomputer 9 can then determine and store in another memory zone 99 the value of the M/R ratio between the digital measuring signals and the digital reference signal, as described herebelow.

In most cases, the variations of this ratio are compared to a "base line" representing a reference state of both samples.

The already mentioned article of Journal de Chimie Physique describes in its annex in FIG. 9 how to obtain a high voltage power supply of a flash tube, that can be quickly recharged, without any risk of re-ignition of the tube at the time of rising voltage. It also describes how to use an auxiliary coil which defines a synchronization pulse, which can be used for instruments 8M and 8R of this invention.

It is preferable to use such a measuring light source as represented by block 1 of FIG. 1. The possibility of applying to the samples to be considered bursts of flashes, which follow each other at a rate that can be as short as on the order of milliseconds, can thereby be achieved. This is interesting, especially for rapidly evolving systems.

Figure 2:
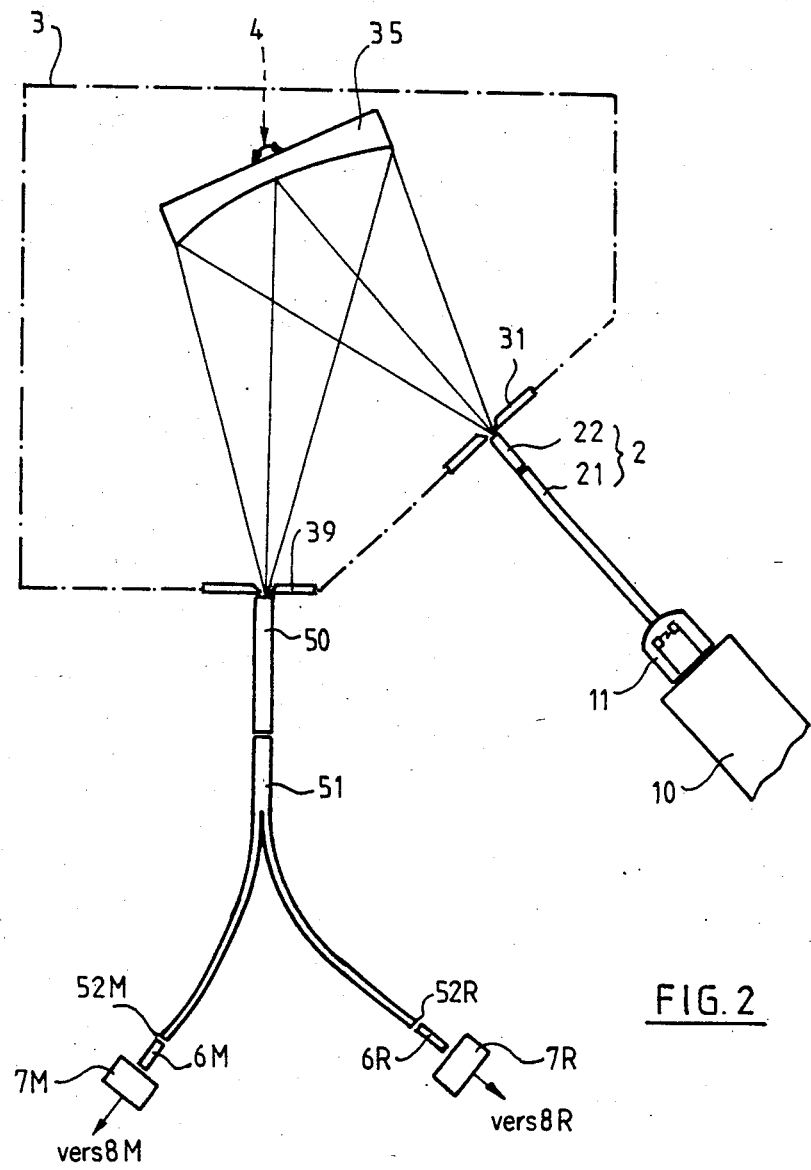
FIG. 2 is a schematic representation of the essentially optical part of the device.

FIG. 2, which goes over some aspects of FIG. 1, shows a xenon flash tube 11, equipped with a power supply 10 which can be the same as the one described in the above mentioned document.

The light of every flash is sent to a bundle of optical fibers 21, preferably disposed with a substantially random distribution, followed by a parallelepipedic light guide 22, which is followed by the inlet slit diaphragm 31 of the monochromator 3. The inlet slit diaphragm 31 is defined by two mechanically adjustable half-slits. The monochromator 3 can be a commercial monochromator equipped with a concave holographic grid, more specifically of the Jobin and Yvon HL type, equipped with a concave 15 cm diameter holographic grid. However, it has been found desirable to modify this monochromator, as shown on FIG. 2, to suppress all mirrors and inner reflection instruments, ordinarily used to obtain in the outlet slit diaphragm an optical image of the inlet slit diaphragm.

The light thus goes directly from the inlet slit diaphragm 31 to the concave holographic grating 35, and comes back after being reflected once onto the outer slit diaphragm 39, which is adjustable like the inlet slit diaphragm 31.

The beam of monochromatic flashes which provides the measuring light, such as it is on the outer slit diaphragm 39, is passed to a parallelepipedic light guide 50, followed by an optical fiber guide forming a double derivation in a "Y" shape, with a substantially random distribution of the optical fibers of the common part towards the two branches. The free ends 52M and 52R of these two branches are applied to two cells 6M and 6R, respectively a measuring cell and a reference cell.

These cells are in their turn followed by photodetectors 7M and 7R.

It has been found that with the optical fibers which are currently available, the use of a parallelepipedic guide such as 50 is essential to obtain a true balanced distribution of the measuring light towards the two samples. This balance is further improved if, at the inlet of the monochromator, a bundle 21 with a random distribution of its elementary fibers is used, thus compensating for the spatial law of distribution of the light which is produced at the inlet of the flash source 11. It is also improved if a parallelepipedic light guide is used. The optical paths of that light guide perfect this compensation, at a level where the measuring light is still polychromatic.

A stepping motor 4 allows adjustment of the position of the concave holographic grid 35 to obtain the monochromatic light of the requested wavelength on the outer slit diaphragm 39.

It has been found that when a fiber 51 in "Y" shape with random distribution, which is commercially available, is used by itself, a flash which is truly statistically balanced between both cells is not obtained.

Although the phenomenon is not completely understood, the applicants believe that this is due to the fact that the random distribution is done on small number of fibers, rather than on individual fibers.

It has been observed that the use of a parallelepipedic light guide 50 between the outer slit diaphragm 39 and the inlet or common body of the optical fiber coupler in "Y" shape 51 ensures a statistically balanced distribution of the light between both cells.

It has also been found that the width of the outer slit diaphragm 39 (or even of the inlet slit diaphragm 31) has a tendency to vary during the photochemical experimentations. If the coupler 51 is located directly after the outer slit diaphragm 39, the result is that the number of active inlet fibers varies as the slit width varies. The use of the parallelepipedic light guide 50 also provides the advantage of eliminating this fluctuation by systematically canalizing the light on the whole inlet opening of the coupler 51.

Photodetectors 7M and 7R are advantageously of a large surface area and wide band. The applicant presently prefers to use silicium photodiodes, such as the photovoltaic cells, model UV 444 BQ of the United States Corporation called EGEG. Such cells present the advantage of operating from ultraviolet to the near-infrared.

Also, since the flash tubes are operational on a wide light band, and since the monochromator can also be adjusted to a rather wide bandwidth, the whole system is able to operate at numerous different wavelengths of light without the need for interchanging any element.

Figure 3:
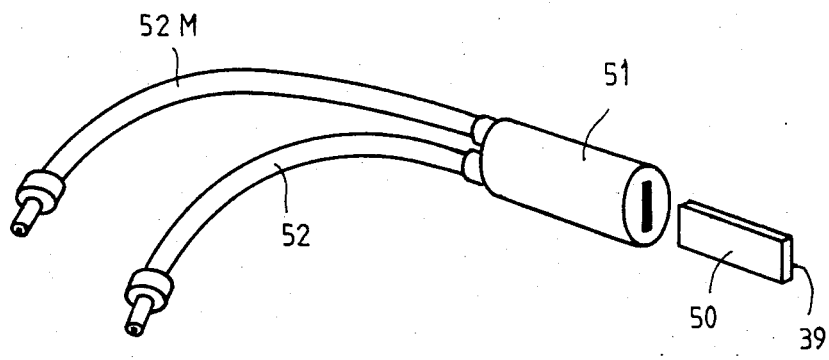
FIGS. 3 and 3A is a detailed schematic representation of examples of experimentation cells used in biology for implementing the invention.
Figure 3A:
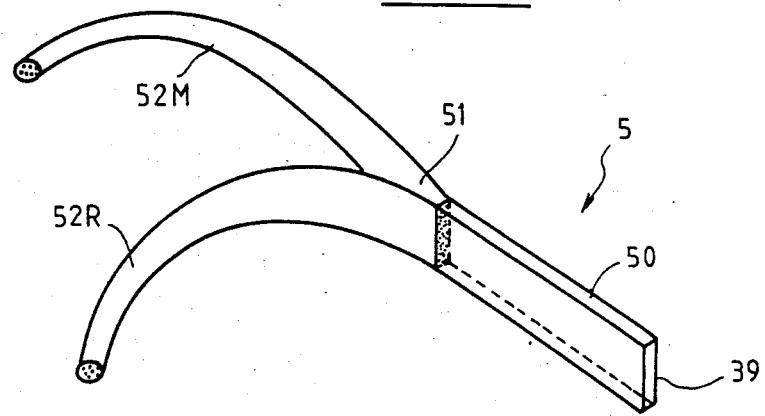

FIGS. 3 and 3A illustrate the optical interconnection of the "Y"-shaped feeder 51 with the parallelepipedic light guide 50. FIG. 3 shows the parts in their actual shape and FIG. 3A is a schematic illustration to better understand their operation.

The main dimensions of these instruments are as follows:

The parallelepipedic guide has a length of 50 mm, a height of 10 mm and a width of 2.5 mm. The active inlet surface 510 of the coupler 51 can measure for example 10×2.5 mm. The outlet of each branch 52 is circular in cross-section with a diameter of 4 mm.

The expression "statistical distribution" when referring to the distributed fibers on the inlet rectangle of the common body 51 of FIG. 3, means that, for a small group of neighboring fibers (ideally on any group of two neighboring fibers), half of these fibers will go into branch 52M, and the other half into branch 52R.

The cells to be used for implementing the invention can be quite different ones. But it is desirable that the side walls of each cell (those which are parallel to the direction of the measuring light) form light guides within the cell. If the walls are themselves light conductive, one should take care that the measuring light be not preferentially transmitted through the wall itself through its thickness.

Figure 4:
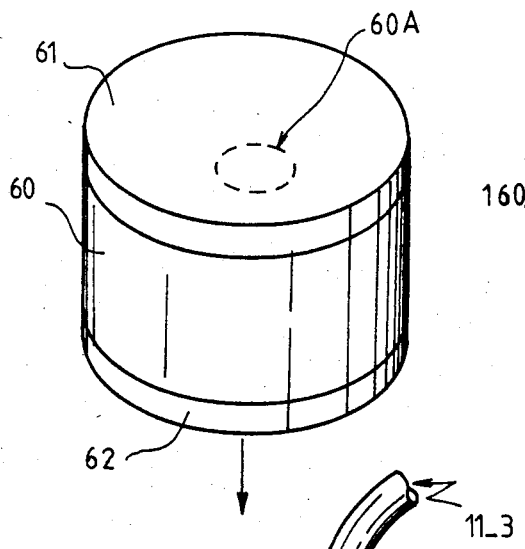
FIGS. 4 and 4A are schematic representations of examples of experimentation cells used in biology for implementing the invention.

The cells can be made of quartz, glass or metal. An example of such a cell is described in the already mentioned article of Journal de Chimic Physique. FIG. 4 shows, schematically, another example. A cylindrical side wall 60 is made of glass or metal. It has at one end an inlet window 61 and at the other end an outlet window 62 made of glued silica. Tubing (not shown) passes through wall 60 to enable the cell to be filled. The beam of measuring light contacts the cell substantially in the middle of the inlet window 61 as indicated by the dotted line 60A, in order to prevent as much as possible any conduction of the measuring light towards the thickness of the wall 60, when the wall is made of glass. If this wall is made of metal, the beam can be larger in cross-section.

Figure 4A:
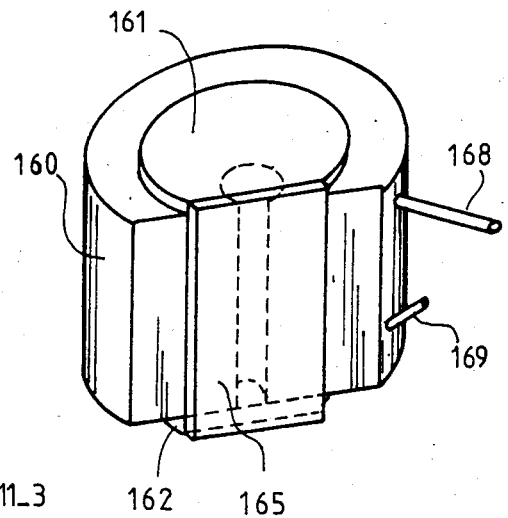

Another example of a cell which can be used in photochemistry, is shown in FIG. 4A. A metal block 150 has generally a substantially cylindrical shape. It is laterally truncated in a direction parallel to its generating line. This truncated face receives a silica window 165, which is glued in place, and through which it is possible to apply an excitation light which is well known by photochemists (see on this matter the already mentioned article of Journal de Chimie Physique).

At the ends, the inlet window 161 and the outlet window 162 are also made of silica and glued onto the metal block 160. The measuring light is applied as indicated by the dotted line to the face 161 of FIG. 4A.

Such a cell can have an inner diameter of 5 mm, for a height of 11 mm. The tubings 168 and 169 are provided with this cell for filling the cell.

It is now better understood that, on the outlet side of the cell, the photodetectors used must have a good quantum yield, a large surface area, and, inasmuch as possible, be free from hysteresis taking into account the fast rate of the flashes.

Figure 5:
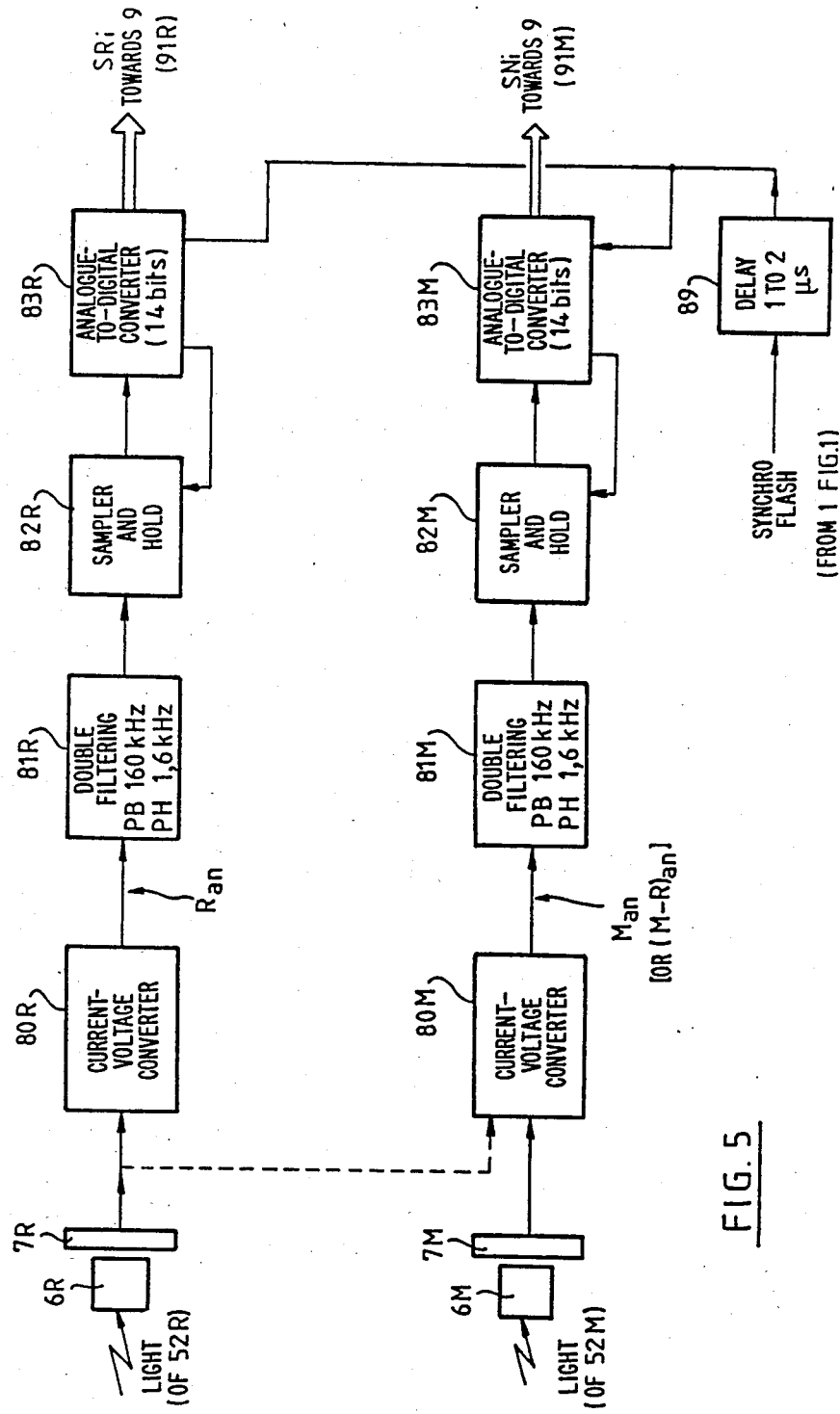
FIG. 5 is a partially detailed schematic representation of the electronics inserted between each cell and the numerical memory which receives the signals corresponding to the cell.

FIG. 5 shows the electronics used according to the invention. Photodetectors 7R or 7M (hereafter the suffix R or M will be omitted, unless it is necessary to mark the difference) are connected first to a current-voltage converter 80, followed by a double filtering circuit 81, then to a sampling and holding device 82, and finally an analog-to-digital converter 83.

A retardation circuit 89 receives the synchronization signal coming from the power supply of the flash source, as already described. It applies to this signal a preset delay, which is, for example, of 1 to 2 microseconds, according to the useful duration of the flash.

During each flash, an analog signal is supplied by photodetectors 7, in the form of a current which is related to the number of photons which hit the photodetector. The stage 80 converts this current into voltage. The voltage is filtered by stage 81, in order to be limited to the band ranging from 1.6 kHz to 160 kHz.

In other words, the double filtering circuit 81 realizes a low-pass time constant of about 1 microsecond, which starts the integration of the photovoltaic signal. The high-pass characteristic of the filter has a time constant of about 100 microseconds, to compensate for possible drifts.

The respective reference and measurement signals before filtering are designated Ran and Man, which are of an analog nature.

These signals are sampled by the sampling and holding devices 82, during their opening time, which is defined by the analog-to-digital converter 83. This converter 83 determines the opening time, the outlet of retardation circuit 89, so that it triggers the sampling at the right time, to take into account the slight fluctuations which appear between the measuring light and the signal that controls it, and to eliminate the tail of the flash.

The operation described up to now, in which the reference and measuring paths are fully separated, can, at least for some applications, require an analog-to-digital converter with a fairly high resolution.

In order to get satisfactory results with a 14 bit resolution for the converter, it is preferable that the current-voltage converter 80M include, as described in the already mentioned publication of the Journal de Chimie Physique, a differential inlet amplifier receiving on one hand the signal from the photodetector 7M, on the other hand the signal from the photodetector 7R. The measurement then operates on a signal (analog, then digital) which corresponds to the difference between the measuring signal and the reference signal. The digital signals $SN_i$ and $AR_i$, which are available at the outlet of FIG. 5, are sent to the microcomputer 9 (FIG. 1).

As previously indicated, the computer 9 calculates the ratio of the $SN_i$ signals to the $SR_i$ signals and compares this ratio to a basic line representing a reference state of both samples. Of course this ratio is either of the form M/R or of the form (M−R)/R.

This invention thus provides a very high sensitivity spectrophotometer, which is furthermore able to operate with an excellent yield and an excellent ratio of signal-to-noise, on the basis of monochromatic flashes of short duration, about 2 microseconds. The integration is done during a duration which is somewhat shorter than one flash, i.e. about 1 microsecond.

A first advantage of the invention lies in the fact that on a microsecond scale, both the chemical reactions which occur in the measuring cell (eventually in the other cell) and the mechanical state of the measuring system can be considered to be fixed. The system is thus free from the very numerous sources of outer disturbances.

Moreover, the monochromator, which is used can have a large opening (F/2). This, added to the geometry of the whole optical device, is particularly favourable to the study of samples with a high cloudiness and high diffusibility, a property which is common to many biological samples. Finally, the use of optical fibers provides for flexibility in the distribution of light.

Another advantage is that a spectral field from 250 nanometers (or less) to at least 800 nanometers can be covered without changing either the grid of the monochromator, or the photodetectors, or even the flash tube.

The width of the detection light band depends essentially on the quality of the slits. It has been possible to establish slits to obtain a bandwidth of about 0.5 nanometer.

Even with very high optical density suspensions (1 to 2), a better sensitivity than $10^{-5}$ absorption units or $1.5 \times 10^{-5}$ in transmission variation can be easily obtained. This sensitivity can be improved by spectrum summation.

On the other hand, the monochromatic measuring and reference beams are available at the ends of optical fibers (present diameter 4 mm), which allows for the use of cells with very diverse shapes and small volumes. It is also particularly easy, as an alternative to what has been described above, to work on solid media, such as, for instance, a leaf of an higher order plant, or a Millipore filter, on which light absorbing substances could be deposited. In this case, the device can operate with its maximum sensitivity ($10^{-5}$ absorption units) in spite of the high absorption and diffusion of the media which are used (Millipore or leaf). Moreover, the use of measuring flashes which are easily triggered by pulses induced by logical circuits favours the automation of the device, which can then be controlled by the microcomputer in charge of processing the digital data.

In certain types of chemical reactions so-called kinetic reactions, starting a reaction implies the mixing of two components (by the so-called "stopped flow" method). The resolution is therefore limited by the mixing duration, which is generally a few milliseconds long. The observation is then made, after the mixing, in a small size cell.

The difficulty that occurs is due to the fact that the optical absorption properties of the medium are caused in two ways:

The first way is for the dynamic chemical reaction to be examined, which constitutes the useful information.

The second way is by the turbulences induced by the mixture, or by other effects, for example variations in light diffusion, which constitute superfluous information. It is desirable to separate this superfluous information from the useful information.

The only known way to perform this separation is by performing a differential double measuring, which means that both cells will be energized separately, with the second cell being energized a short time after the first cell with light of a different wavelength from light used to energize the first cell. It is then possible to obtain the specific spectrum of the kinetic chemical reaction. Up to the present time, two monochromators must be operated to perform this separation, which is as heavy and expensive as it is delicate to implement.

The applicants have observed that this invention supplies a much more satisfactory solution for studying the kinetics of chemical reactions.

For this purpose, the monochromator has to be supplied with many inlet slit diaphragms, which are respectively energized by as many light guides and as many xenon tubes together with their power supplies.

As for the rest of the apparatus, the monochromator is kept along with the connection of its outlet slit diaphragm towards the measuring cells, which provides considerable experimental simplification.

The duration of each flash being of 2 microseconds, it is then possible to have two flashes following one another with a separation of a few tens of microseconds. This time is necessary for the acquisition of digital values. This is done in order to sequentially analyze the measuring and reference cells with two monochromatic beams of different wavelengths, following one another at a very fast rate as compared with both the chemical and mechanical dynamic features of the system.

Figure 6:
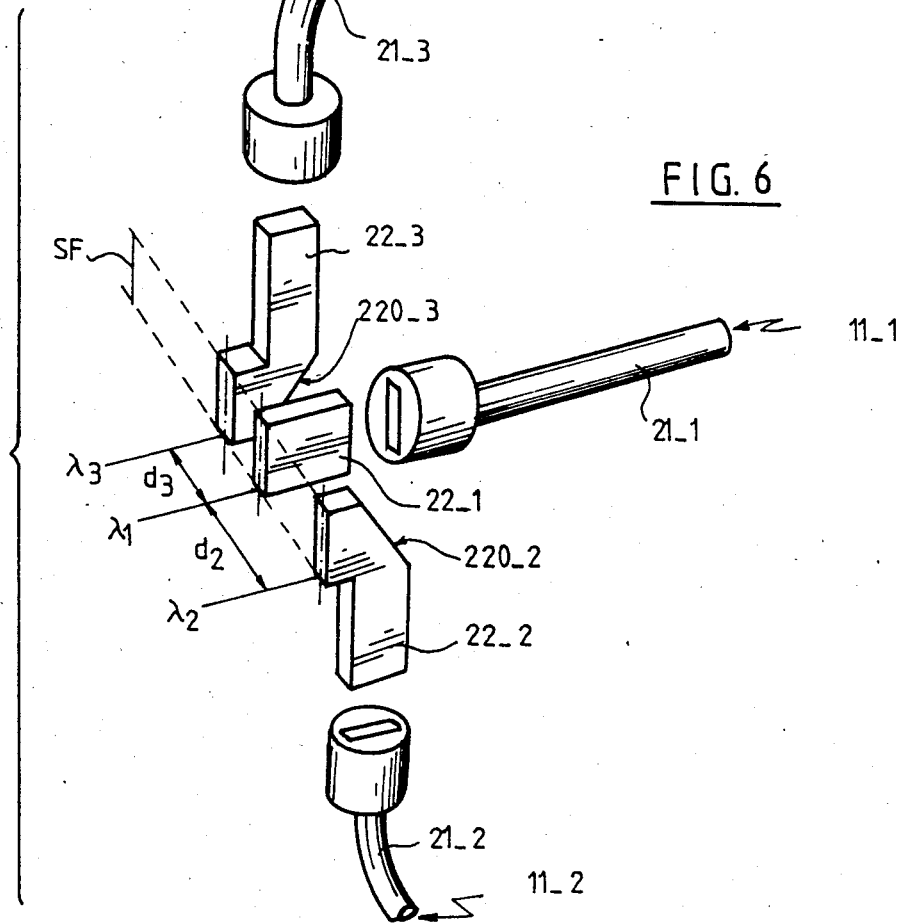
FIG. 6 is the principle schematic representation of a device according to the invention, in which the monochromator includes three inlet slit diaphragms.

FIG. 6, which will be described now, shows an embodiment of the present invention, which is able to operate sequentially on many beams with different wavelengths.

In FIG. 6, the plane SF represents the inlet focal surface of the concave holographic grid 35, at the level of which the different inlet slit diaphragms will be chosen. As in the previous embodiment, an optical fiber beam 21-1 is lighted by a xenon lamp 11-1. The active rectangle of its outlet face lights a parallelepipedic light guide 22-1 made of silica.

In this embodiment, the outlet face of the guide 22-1 defines the width of inlet slit diaphragm of the monochromator. The slit diaphragm is then not more adjustable.

The wavelength corresponding to the position of the guide 22-1 on the focal surface SF is noted as $\gamma_1$.

At a small distance $d_2$, and on the same focal surface, is located the outlet face of a light guide 22-2, which also has a parallelepipedic shape, but in two parts, at a right angle one from the other, and coupled by an angle deflector 220-2. The set consists, primarily, of a single block, and the angle deflector is plainly a face at 45° coated on the outside with metal. The inlet face of the guide 22-2 is coupled to the active outlet surface of a bundle of fibers 21-2 with random distribution supplied by a xenon lamp 11-2.

In an identical manner, the lamp 11-3 energizes the randomly distributed fibers 21-3, which supply another light guide 22-3 with an angle deflector 220-3. The outlet face of the latter defines a third inlet slit diaphragm on the focal surface SF, at a distance $d_3$ of the slit defined by the outlet of the guide 22-1.

Three different wavelengths are thus available $\gamma_1$, $\gamma_2$, and $\gamma_3$, which can be optionally applied to the monochromator.

Although the widths of the slits are not adjustable, it is still possible to vary them by exchanging the light guides 22 with other guides which have either narrower or wider outer faces.

It is desirable that the wavelengths variations between the various measuring light beams used be not too large.

It should be noted that even if the bandwidth obtained with one of the beams is slightly wider than the other one, this property is not incompatible with the experimental use which can be done of many wavelengths.

What is claim is:

1. A differential spectrophotometer, comprising two sample locations, optical means for applying to the two samples monochromatic measuring light, photodetectors for selectively collecting the light transmitted through each one of the two samples, and electronic means for comparing the quantities of transmitted light thus measured by the two photodetectors, said optical means distributing the measuring light statistically balanced to the two samples and including a flash source illuminating an inlet slit diaphragm of a monochromator with a concave holographic grid, a parallelepipedic light guide optically coupled to an outer slit diaphragm of the monochromator and followed by a Y-shaped guide of optical fibers where the optical fibers are substantially randomly distributed between two branches of the Y providing the statistical balanced light.

2. A differential spectrophotometer according to claim 1 wherein said flash source is connected to the inlet slit diaphragm of the monochromator by a beam of the optical fibers with a substantially random distribution, said beam being followed by a parallelepipedic light guide.

3. A differential spectrophotometer according to claim 1 or 2, wherein said monochromator is arranged with at least one inlet slit diaphragm respectively coupled by optical-fiber beams to at least one flash tube in order that various beams with neighboring wavelengths be optionally available on the outer slit diaphragm of the monochromator.

4. A differential spectrophotometer according to claim 3, wherein at least some of the light guides located at the inlet of the monochromator include an angle deflector.

5. A differential spectrophotometer according to claim 4, wherein the inlet slit diaphragms of the monochromator are essentially defined by the light guides.

6. A differential spectrophotometer according to claim 5, wherein the light photodetectors are silicium photodiodes of large surface area, for collecting the light transmitted through a solid angle and with a high quantum yield.

7. A differential spectrophotometer according to claim 6, wherein said photodiodes are sensitive to wavelengths ranging from ultraviolet to near-infrared.

8. A differential spectrophotometer according to claim 7, wherein said electronic means includes current-voltage converting means, associated with double filtering means having a low-pass effect under a frequency of 100 KHz, and a high-pass effect above a frequency of one kHz.

9. A differential spectrophotometer according to claim 8, wherein said electronic means also includes, for each measurement corresponding to each sample sampling and holding means associated with an analog-to-digital converter, the electronic means being controlled each time a flash is omitted by a retardation circuit which receives a synchronization pulse coming from the flash source.

10. A spectrophotometer according to claim 9, wherein said electronic means includes calculation means which receives the outputs from two analog-to-digital converters to determine therefrom a ratio which is then subjected to digital processing said processing including the comparison of said ratio to a baseline reference which represents a state of both samples.

11. A differential spectrophotometer according to claim 10, wherein one of the samples is a working sample (M) while the other one is a reference sample (M).

12. A differential spectrophotometer according to claim 11, wherein said current-voltage converting means associated with the reference sample operates on the output from the corresponding photodetector, a current-voltage converting means corresponding to the working sample operates on the difference between the output from the photodetector associated with the working sample and the output from the photodetector associated with the reference sample.

13. A differential spectrophotometer according to claim 11, wherein said samples are submitted to photochemical energized light.

14. A differential spectrophotometer according to claim 13, further comprising cells arranged so that their walls form a light guide, at least for the measuring light and said samples being held in said cells.

15. A differential spectrophotometer according to claim 14, wherein each cell is metal and is opened on one side to form a window through which energizing light can pass.

* * * * *